United States Patent
Boe et al.

(12) 
(10) Patent No.: US 6,225,300 B1
(45) Date of Patent: May 1, 2001

(54) TNF RECEPTOR AND STEROID HORMONE IN A COMBINED THERAPY

(75) Inventors: Alessandra Boe; Francesco Borrelli, both of Rome (IT)

(73) Assignee: Applied Research Systems ARS Holding NV, Rome (IT)

( * ) Notice: Subject to any disclaimer, the term of this patent is extended or adjusted under 35 U.S.C. 154(b) by 0 days.

(21) Appl. No.: 08/983,223

(22) PCT Filed: Jul. 14, 1995

(86) PCT No.: PCT/EP95/02767

§ 371 Date: Feb. 27, 1998

§ 102(e) Date: Feb. 27, 1998

(87) PCT Pub. No.: WO97/03686

PCT Pub. Date: Feb. 6, 1997

(51) Int. Cl.$^7$ .......................... A61K 38/19; A61K 31/56
(52) U.S. Cl. ................. 514/171; 514/2; 514/12; 514/169; 514/170
(58) Field of Search .................. 514/2, 12, 252, 514/169, 540, 170, 560, 310, 171; 530/350; 435/69.4

(56) References Cited

FOREIGN PATENT DOCUMENTS

| | | |
|---|---|---|
| 92512528 | 11/1992 | (EP) . |
| 92 13095 | 8/1992 | (WO) . |
| 94 06476 | 3/1994 | (WO) . |
| 95 03827 | 2/1995 | (WO) . |

OTHER PUBLICATIONS

Stedman's Medical Dictionary, 26 Ed. Williams & Wilkins, Baltimore, pp 1608–1609, 1995.*

H.D. Danenberg, et al., "Dehydroepiandrosterone protects mice from endotoxin toxicity and reduces tumor necrosis factor production", *Antimicrob Agents Chemother*, vol. 36, No. 10, 1992, pp. 2275–2279.

R.F. Van Vollenhoven, et al., "In patients with Systemic Lupus Erythematosus, treatment with oral dehydroepiandrosterone restores abnormally low in vitro production of IL–2, IL–6 and TNF–alpha", *Arthritis & Rheumatism*, vol. 37, No. 9, suppl., 1994, p. 407.

J.Y. Yang, et al., "Inhibiton of HIV–1 latency reactivation by dehydroepiandrosterone (DHEA) and an analog of DHEA", vol. 9, No. 8, 1993, pp. 747–754.

M. Cutolo, et al., "Immunomodulatory mechanisms mediated by sex hormones in rheumatoid arthritis", Annals of the New York Academy of Sciences, Basis for Cancer Management. Conference on Propedeutics to Cancer Management, Erice, Italy, Apr. 1–6, 1995. vol. 784, 1996. pp. 237–251.

F.C. Kull, "Reduction in tumor necrosis factor receptor affinity and cytotoxicity by glucocorticoids", *Biochem., Biophys. Res. Commun.*, vol. 153, No. 1, 1988, pp. 402–409.

S.M. Opal, et al., "Tumor Necrosis Factor Receptor–Fc Fusion Protein (sTNFR:Fc) in the treatment of experimental Pseudomonas sepsis", Program and Abstracts of the Interscience Conference on Antimicrobial Agents and Chemotherapy, vol. 33, No. 0, 1993, p. 378.

E. Tartour, et al., "Anti–cytokines: promising tools for diagnosis and immunotherapy", *Biomed Pharmacother*, vol. 48, No. 10, 1994, pp. 417–424.

D. Russell, et al., "Synergistic protection against lethal endotoxemia by treatment with Interleukin–1 receptor antagonist and tumor necrosis factor binding protein", Lymphokine and Cytokine Research, vol. 12, No. 5, 1993, p. 377.

The Merck Manual, 16th ed., Robert Berkow, Editor–in–Chief, Merck & Co., Inc. pp. 71, 2664 and 2780, 1992.*

* cited by examiner

*Primary Examiner*—F. T. Moezie
(74) *Attorney, Agent, or Firm*—Ostrolenk, Faber, Gerb & Soffen, LLP

(57) ABSTRACT

The present invention relates to the use of a TNF Receptor together with a steroid hormone to produce a pharmaceutical composition for the treatment of lethal bacterial and viral infections as well as autoimmune and inflammatory diseases. It also relates to said pharmaceutical compositions for the simultaneous, separate or sequential use of its active ingredients for the above specified treatment. In particular, it relates to the use of TBP-1 together with dehydroepiandrosterone (DHEA) or its metabolites to produce a pharmaceutical composition for the treatment of septic shock.

8 Claims, 3 Drawing Sheets a = significantly different from r-hTBP-1 group ($\chi^2$-test)
b = significantly different from control group ($\chi^2$-test)

TNF RECEPTOR AND STEROID HORMONE IN A COMBINED THERAPY

FIELD OF THE INVENTION

The present invention relates to the use of a TNF Receptor together with a steroid hormone to produce a pharmaceutical composition for the treatment of lethal bacterial and viral infections as well as autoimmune and inflammatory diseases. It also relates to said pharmaceutical compositions for the simultaneous, separate or sequential use of its active ingredients for the above specified treatment.

In particular, it relates to the use of TBP-1 together with dehydroepiandrosterone (DHEA) or its metabolites to produce a pharmaceutical composition for the treatment of septic shock.

BACKGROUND OF THE INVENTION

Septic shock as a consequence of Gram-negative bacteremia or endotoxemia remains a critical clinical condition in spite of adequate antibiotic therapy.

It is now known that the lethal consequences of septic shock results from an exaggerated host response, mediated by protein factors such as TNF and interleuldn 1 (IL-1), rather than from the pathogen directly.

Tumour necrosis factor (TNF) is a cytokine produced mainly by activated macrophages, which elicits a wide range of biological effects. These include an important role in endotoxic shock and in inflammatory, immunoregulatory, proliferative, cytotoxic and antiviral activities.

The induction of the various cellular responses mediated by TNF is initiated by its interaction with two distinct cell surface receptors of approximately 55 kDa (also called TNF-R1) and 75 kDa (also called TNF-R2). The extracellular soluble portions of these receptors, called respectively TBP-1 (TNF Binding Protein-1) and TBP-2 (TNF Binding Protein-2), have been isolated and cloned (see EP Patents 308 378, 398 327 and EP patent Application 433 900).

Several studies in animal models of TNF-mediated endotoxic shock indicated that both anti-TNF antibodies and soluble TNF-receptor are able to counteract the lethal effects induced (see for example: Bentler, B et al., Science, 229:869 (1985), Lesslauer, W. et al., Eur. J. Immunol., 21:2883 (1991), Evans, T. J. et al. J. Exp. Med., 180:2173 (1994) and Mohler K. M. et al., J. Immunol. 151:1548 (1993)).

The in vivo protective effects of urinary as well as recombinant TBP-1 (derived from both CHO and *E. Coli* cells) in experimental models of septic shock have already been demonstrated (see Bertini. R. et al., Eur. Cytokine Netw. 4(1):39 (1993) and Ythier A., et al., Cytokines. 5:459 (1993)).

DHEA (INN: Prasterone) is an adrenocortical steroid hormone which is an intermediate in the biosynthesis of other hormones including testosterone and estradiol-17β.

The precise biological functions of DHEA are still unclear. Experimental and epidemiological data suggest an inverse relationship between low levels of DHEA in serum and morbidity from atherosclerotic cardiovascular disease (see Barret-Connor, D. et al., N. Engl. J. Med. 315:1519 (1986)), cancer (see Gordon, G.B., et al., Cancer Res. 51:1366 (1991)) and immunodeficiency virus (HIV) infection (Villette. J. M. et al. J. Clin. Endocrinol. Metab. 70:572 (1990)).

An immunomodulating activity of this drug has also been reported; in particular. DHEA has been shown to prevent the development of systemic lupus erythematosus in a mouse model (Lucas, J. et al. J. Clin. Invest. 75:2091 (1985)).

It has been demonstrated that DHEA regulates the systemic resistance against lethal viral infections induced by different viruses: coxsackievirus B4 (as reported in Loria. R. M. et al., Ann. N.Y. Acad. Sci. 293), herpes virus type 2 (see Loria, R. M. et al., J. Med. Virol., 26:301 (1988)), West Nile virus (a neurovirulent Sindbis virus) and Semliki Forest virus (as reported in Ben-Nathan, D. et al. Arch. Virol. 20:263 (1989)).

It has also been reported that DHEA has similar protective effects against a lethal bacterial infection induced by *Enterococciis faecalis* (see Loria. R. M. et al. in Symposium Pharmaco-Clinique, Roussel-Uclaf 9:24 (1989)).

Danenberg. H. D. et at. (Antimicrob. Agents Chemother. 36:2275 (1992)) reported that DHEA has the capability of protecting mice from septic shock induced by lipopolvsaccharides (LPS) alone or by Tumor Necrosis Factor alpha (TNF-α) in combination with D-Galactosamine. LPS administration resulted in high levels of TNF-α, a response that was significantly blocked by DHEA, both in vivo and in vitro.

DISCLOSURE OF THE INVENTION

The main object of the present invention is the use of a TNF Receptor in combination with a steroid hormone to produce a pharmaceutical composition for the treatment of lethal bacterial and viral infections as well as autoimmune and inflammatory diseases. The TNF Receptor and the steroid hormone can be administered simultaneously, separately or sequentially.

The Applicants have, in fact, found that in such treatment there is a synergic effect between the two active ingredients.

Another object of the present invention is, therefore, the method for treating lethal bacterial and viral infections as well as autoimmune and inflammatory diseases by administering simultaneously, separately or sequentially an effective amount of TNF Receptor and an effective amount of a steroid hormone, together with a pharmaceutically acceptable excipient.

A further object of the present invention are the pharmaceutical compositions containing a TNF Receptor and a steroid hormone, in the presence of one or more pharmaceutically acceptable excipients, for the simultaneous, separate or sequential administration of its active ingredients in the treatment of lethal bacterial and viral infections as well as autoimmune and inflammatory diseases.

In case of separate or sequential use of the two active ingredients, the pharmaceutical compositions of the invention will consist of two different formulations, each comprising one of the two active ingredients together with one or more pharmaceutically acceptable excipients.

The administration of such active ingredients may be by intravenous, intramuscular or subcutaneous route. Other routes of administration, which may establish the desired blood levels of the respective ingredients, are comprised by the present invention.

Non-limitative examples of pathologies, in which the above active ingredients are indicated, are the following: septic shock, AIDS, rheumatoid arthritis, lupus erythematosus and multiple sclerosis. Particularly preferred is the treatment of septic shock.

The TNF Receptor is preferably selected between the extracellular soluble domain of TNF-R1, i.e. TBP-1, and the extracellular soluble domain of TNF-R2, i.e. TBP-2. TBP-1 is particularly preferred. Recombinant human TBP-1 (r-hTBP-1) is advantageously used according to the invention.

The steroid hormone can be both a corticosteroid or an androgen. Preferably, it is an androgen. More preferably, it is DHEA or one of its metabolites, dispersed in a suitable medium, for example a phospholipid emulsion or carboxymethyl cellulose or polyvinylpirrolidone.

Therefore, a preferred embodiment of the invention consists in the combined use of r-hTBP-1 and DHEA in the treatment of septic shock. In this case, the Applicant has found that it is possible to reduce at least four times the effective dose of r-hTBP-1.

The above effect has been showed with in in vivo experiments in mice.

In particular, a murine model has been used in the present invention, according to which septic shock is induced by administering lipopolysaccharides (LPS) in combination with D-Galactosarmine.

For the human therapy, the preferred doses of the active ingredient are 20 mg of r-hTBP-1 and 80 mg of DHEA, preferably divided into four administrations in a 24-hours period.

The invention will now be described by means of the following Examples, which should not be construed as in any way limiting the present invention. The Examples will refer to the Figures specified here below.

BRIEF DESCRIPTION OF THE DRAWINGS

In FIG. 2a and 2b are shown the results observed after 24 and 48 hours (respectively) after the inoculum of LPS+D-Galactosamine.

EXAMPLE 1

LPS+D-Galactosamine-induced Septic Shock Model

Figure 1:
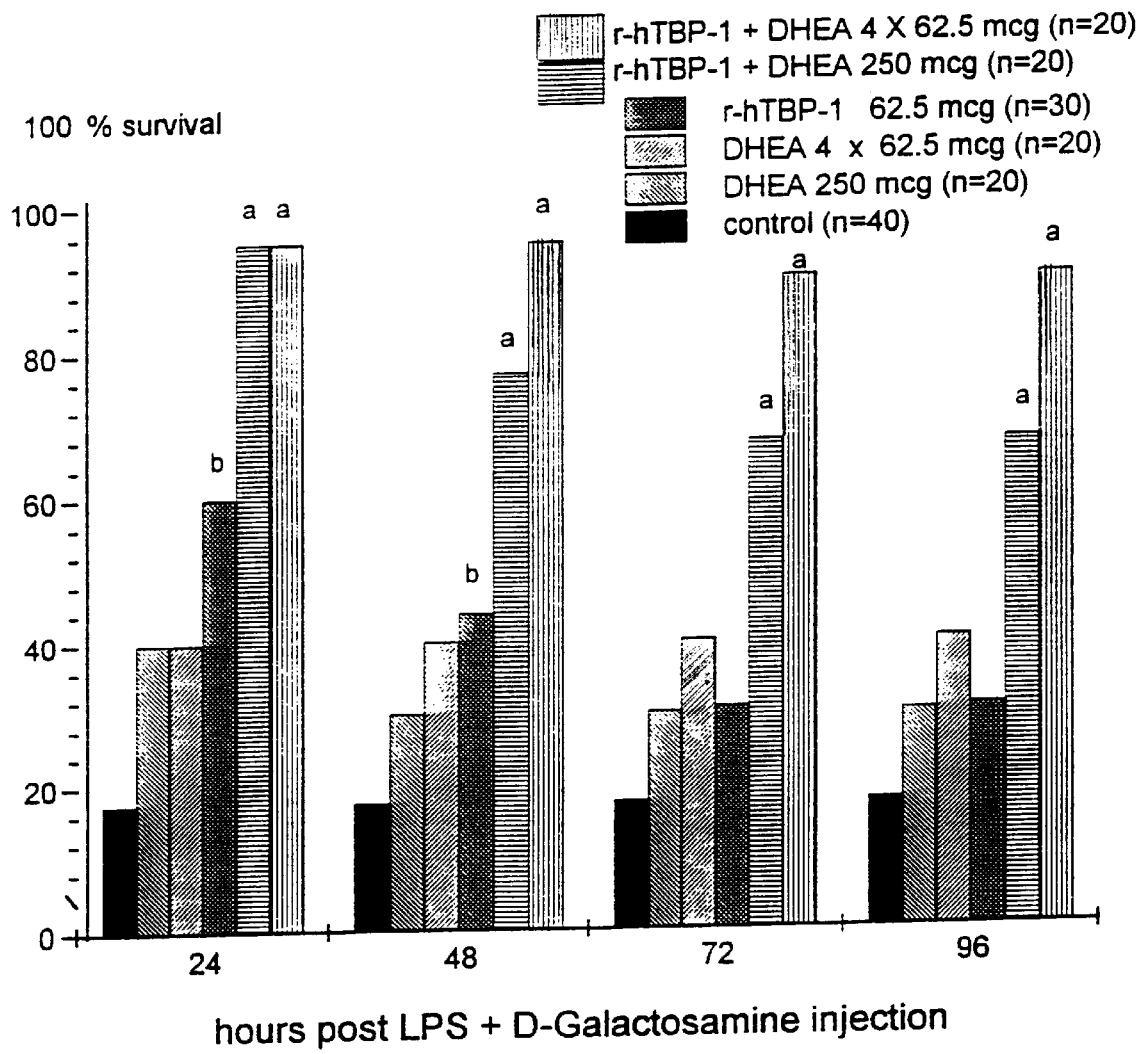
FIG. 1: Protective effects of CHO r-hTBP-1 (62.5 μg/mouse) in combination with single (250 μg/mouse) or repeated injections (4×62.5 μg/mouse) of DHEA in the experimental murine septic shock are shown.

The experiments were carried out in vivo on mice. The septic shock was induced by an i.p. administration of a mixture of LPS (0.1 μg/mouse) and D-Galactosamine (18 mg/mouse).

The treatment schedule for r-hTBP-1 based on repeated administrations (the total dose was divided into 4 administrations given at time 0 and 3, 6 and 24 hours after), was adopted. CHO r-hTBP-1 was tested, alone or in combination with DHEA, at dose levels of 62.5 and 125 μg/mouse (total dose).

Assessment of the Effects of DHEA in the LPS+D-Galactosamine Model

DHEA was tested both in a single administration injected i.p. one hour before and contemporaneously to the septic shock-inducing agent at doses encompassed between 100 and 2,000 μg/mouse and in repeated treatment with the total dose (250 μg/mouse) divided into 4 injections given within 24 hours.

Assessment of the Effects of DHEA in Combination with r-hTBP-1

The above treatment schedules of DHEA (doses from 250 to 1,500 μg/mouse) were followed also in combination with r-hTBP-1 which was tested at the total dose arving from 62.5 to 125 μg/mouse (divided into 4 administrations).

Materials

Animals

SPF female BALB/c inbred mice, 6–8 weeks (about 18–20 g b.w.), from Charles River were used throughout the whole study after an acclimatisation period of at least 7 days.

Unless otherwise specified, in all the experiments the mice were randomly divided into groups of 10 animals each.

Test Drugs

CHO recombinant human TBP-1 produced according to the known methods in the field of biotechnology.

The protein mass of the r-hTBP-1 bulk was determined by the Lowry method before starting the experiments.

E. Coli lipopolysaccharides 055:B5 supplied by Sigma.

D-(+)-Galactosamine hydrochloride, 99% supplied by Janssen.

Dehydroepiandrosterone supplied by Sigma.

Reagents

Sodium chloride 0.9% (Saline), manufactured by Baxter.

Phospholipid emulsion (PLE) composed of phosphatidyl choline (71%), phosphatidyl ethanolamine (16%), lysophosphatidyl choline (7.5%), sphingomyelin (5%) and phosphatidic acid (0.3%).

Methods

Septic Shock Model (LPS+D-Galactosamine model)

Both substances were dissolved in saline. The mixture of LPS (0.1 μg/mouse) and D-Galactosamine (18 mg/mouse) was prepared by mixing equal volumes of these substances. The mixture was subsequently injected to animals by the i.p. route. This dose was selected under precious experiments as that inducing around 80% mortality calculated as the number of dead vs. total number of mice for each group. The lethality was monitored after 24, 48, 72 and 96 hours and at day 7 post-treatment.

Treatment Schedule for r-hTBP-1

The drug was diluted in saline and injected by repeated administrations, i.e. i.v. immediately before the inoculum of LPS plus D-Galactosamine and s.c. 3, 6 and 24 hours later.

Treatment Schedules for DHEA

The effects of DHEA, alone or in combination with r-hTBP-1, were assayed after single i.p. administrations at different times in respect to LPS+D-Galactosamine injection; in particular, it was administered 1 hour before and contemporaneously to the septic shock-inducing agent.

A repeated treatment schedule was also investigated in which DHEA was administered at time 0 (septic shock induction) and 3, 6 and 24 hours later. DHEA was initially vehicled in a mixture of 2.5% alcohol and 10% rabbit serum in saline. To improve the solubility and standardise the preparation, the steroid was successively dispersed in a mixture of 2.5% alcohol and 10% phospholipid emulsion in saline.

Data Evaluation

The primary end point was the survival rate at 48 hours after induction of septic shock. The comparison of the effects of each treatment group vs. controls and among treatment groups was effected by Fisher's exact test, one-tailed. The same comparison was also performed at the other time points. The results in each treatment group were expressed as percent survival.

Results

DHEA Administered 1 Hour before LPS+D-Galactosarnine

The results of the DHEA dose-range finding experiments are reported in Table 1. No protective effects were exerted by this substance up to 1,000 1 μg/mouse; by contrast, statistically significant protective effects were obtained at higher doses with a complete protection at 2,000 μg/mouse at all time points considered.

When a suboptimal dose of CHO r-hTBP-1 (125 μg/mouse), inducing about 50% survival, was administered in combination with two suboptimal doses of DHEA (1,000 and 1,500 μg/mouse), an additive effect between the two substances was observed (Table 2). The result of the combination with the highest DHEA dose, where a 100% survival rate was obtained, is significantly different from that of the r-hTBP-1 group (50%) and DHEA group (40%).

DHEA Administered Contemporaneously with LPS+D-Galactosamine

The results obtained in the DHEA dose-range finding test, where the substance, diluted in saline 10% rabbit serum, was administered contemporaneously to septic shock induction are reported in Table 3.

Although a clear dose-effect relationship has not been found a higher protection was produced by 1,000 μg DHEA in comparison to what observed with the same dose by the previous treatment schedule (DHEA administered 1 hour before).

The combination of 62.5 μg/mouse of r-hTBP-1 with 250 μg/mouse of DHEA induced a slightly higher protection (60%) in respect to the single treatments (20% and 30% for r-hTBP-1 and DHEA, respectively, see Table 4). When the same combination was vehicled in a 10% phospholipid emulsion, to improve the solubility of DHEA, a significantly higher survival was obtained compared to DHEA and r-hTBP-1 alone (Table 4) at 24 hours which, however, successively decreased.

Repeated Administrations of DHEA after LPS+D-Galactosamine

Comparable results (30 and 40% survival rate at 48 hours) were obtained when a dose of 250 μg/mouse of DHEA was administered as a single injection (Table 5, group D) or divided into 4 inocula (given at 0, 3, 6 and 24 hours from septic shock induction, group E), respectively. Similarly, no statistically significant differences were found when the animals were injected the combination of r-hTBP-1 and DHEA with the latter administered either as a single inoculum (Table 5, group F) or divided into 4 injections (Group G).

Due to the high survival rate obtained in the r-hTBP-1 group, an additive effect is not evident in these tests after 24 and 48 hours where the combination-treated groups were significantly different only from control and DHEA groups.

However, it has to be stressed that the combined therapy induced a more prolonged survival in respect to the r-hTBP-1 group alone since a statistically significant difference was found after 72 and 96 hours.

FIG. 1 reports the data obtained combining the results of the three experiments reported in Tables 4 and 5 in which the dose of 250 μg/mouse of DHEA was injected as a single inoculum or divided into 4 inocula (62.5 μg each).

Figure 2:
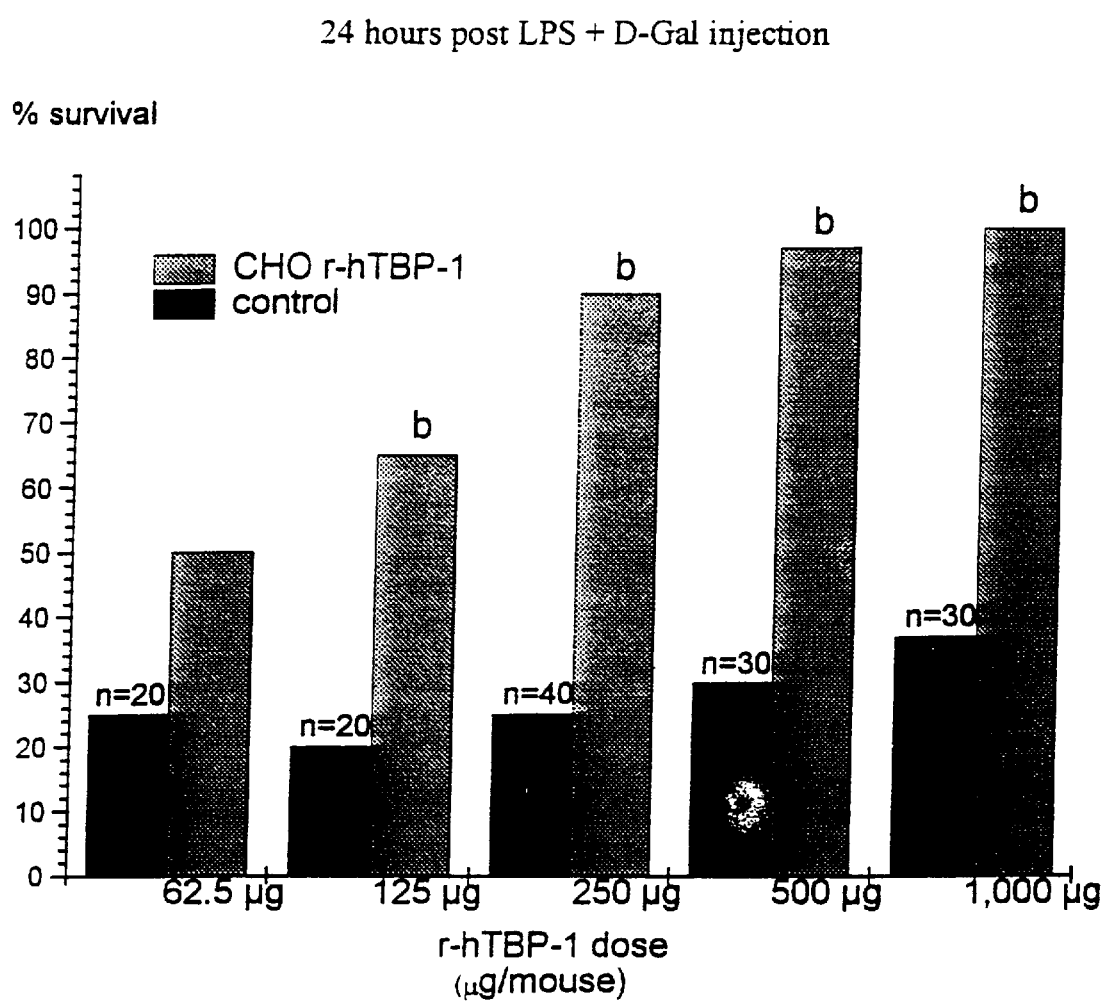
FIG. 2: Protective effects of different doses of CHO r-hTBP-1 in the experimental murine septic shock induced by LPS+D-Galactosamine are shown for comparative purposes. The number of mice in the r-hTBP-1 groups is the same as that reported for the corresponding control groups.
Figure 2:
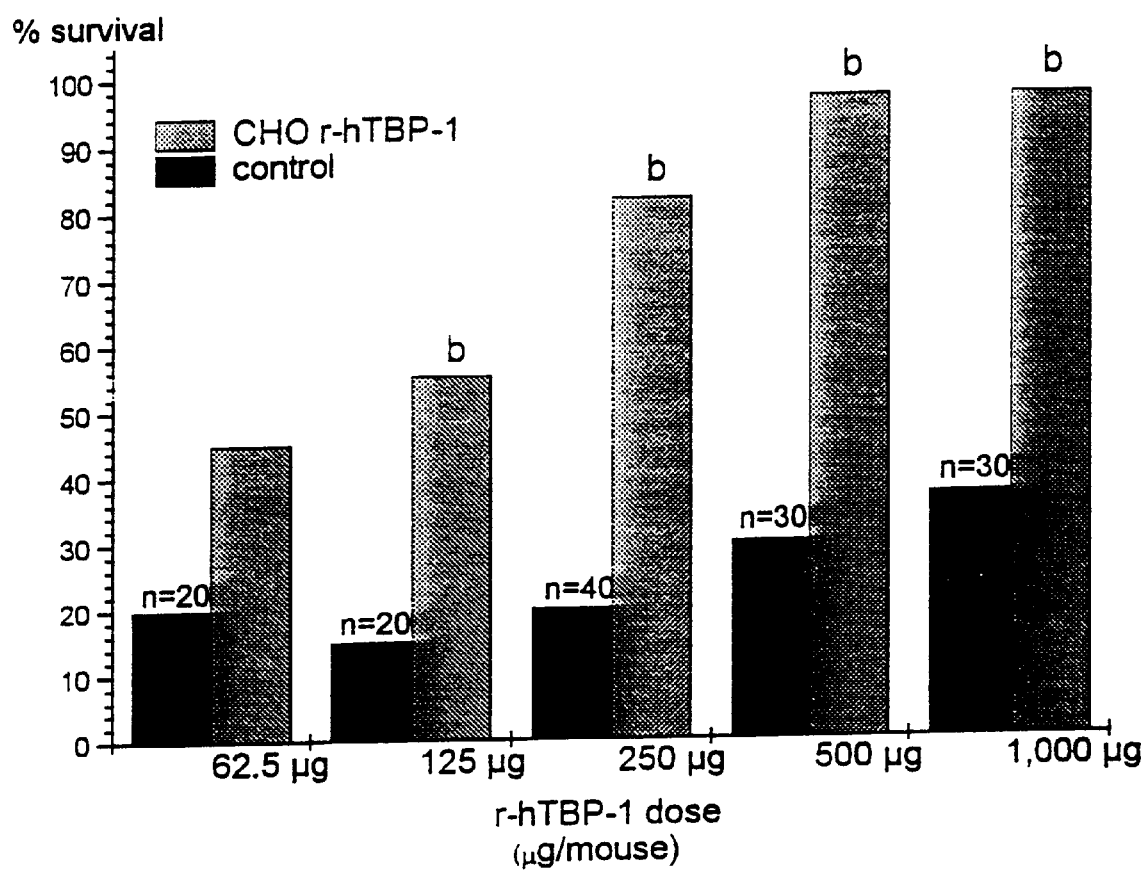

FIG. 2 reports, for comparative purposes, the effects of different doses of CHO r-hTBP-1 alone in the experimental murine septic shock induced by LPS+D-Galactosamine. The number of mice in the r-hTBP-1 groups is the same as that reported for the corresponding control groups. In FIG. 2a and 2b are shown the results observed after 24 and 48 hours (respectively) after the inoculum of LPS+D-Galactosamine.

In all the experiments, percent survival values were calculated using the survival Tables for the follow up studies (Armitage P., Cap. XIV, Tavole di sopravvivenza in Statistica Medica. Feltrinelli, Milano). The $\chi^2$-test was applied to each observation time by comparing the DHEA+r-hTBP-1 groups to the other groups.

In addition to showing that at all time points the combined therapy is significantly different from control and DHEA groups, this analysis confirmed that more prolonged survival times were obtained with the combined treatment in respect to r-hTBP-1 alone. Although no statistical difference between the two treatment combinations has been found, a trend to a more sustained protection can be observed when both drugs were divided into four injections, which is reflected by the different levels of significance at different time-points (Table 6).

Conclusions

A significant protection from death (70% survival) was found with at least 1,500 μg/mouse of DHEA, injected 1 hour before LPS+D-Galactosamine, which confirm literature data.

When suboptimal doses of DHEA (1,000 and 1,500 μg/mouse) and of r-hTBP-1 (125 μg/mouse, total dose) were combined, additive effects (90–100% survival) were produced, compared to 0–40% and 50% with the two doses of DHEA and of r-hTBP-1, respectively.

Similar results were obtained even with lower doses of DHEA (250 μg/mouse) in combination with r-hTBP-1 (62.5 μg/mouse) (90–100% survival), which also provided a more prolonged protection (up to 96 hours) in respect to r-hTBP-1 alone, both when DHEA was injected contemporaneously to LPS+D-Galactosamine in a single inoculum (250 μg/mouse) or when the same dose was divided into 4 inocula (62.5 μg/each) injected at times 0, 3, 6 and 24 hours after septic shock induction.

The present findings are of particular relevance in showing that a combined treatment of r-hTBP-1 with DHEA allows one to reduce the dose of r-hTBP-1 by at least four times.

EXAMPLE 2

Example of Pharmaceutical Manufacturing

A) r-h-TBP-1

Materials

Pure saccharose Ph EurBP. Ph Nord, NF, (Merck); $H_3PO_4$ Suprapur (Merck); NaOH for analysis (Merck); water for injectable.

Vials DIN 2R (borosilicate glass type I), rubber closures (Phamagummi W1816 V50) and Aluminium rings and Flip-off caps (Pharma-Metal GmbH) are used as containers.

Preparation of r-hTBP-1 Solution Containing Saccharose (for 1,000 vials each containing 5 mg of r-hTBP-1) Saccharose (30.0 g) and $H_3PO_4$ (1.96 g) are dissolved into water for injectables (800 ml) in order to obtain the starting saccharose solution.

The bulk of r-hTBP-1 (5 g) is added to the saccharose solution that, after the pH has been adjusted at 7.0 by means of 2.5 M NaOH, is brought to the final volume of 1,000 ml. The solution is filtered through a 0.22 μm Duarapore sterile filter (Millipore). During the process, the solution temperature is kept between 4° and 8° C.

Filling up and Lyophilisation

The vials are filled up with 1 ml of r-hTBP-1 sterile solution, transferred to the freeze dryer and cooled at −45° C. for 6 hours. The lyophilisation is started at the temperature of −45° C. with a vacuum of 0.07 mBar. The heating is performed according to the following scheme: 10° C. for 12 hours; then +35° C. until the end of the cycle.

B) DHEA

Materials

Pure Mannitol Ph Eur. BP. FU. USP. FCC. E241 (Merck): $H_3PO_4$ Suprapur (Merck); NaOH for analysis (Merck); water for injectable.

Vials DIN 2R (borosilicate glass type I), rubber closures (Pharmagummi W1816 V50) and Aluminium rings and Flip-off caps (Pharma-Metal GmbH) are used as containers.

Preparation of DHEA Solution Containing Mannitol (for 1,000 vials containing 10 mg of DHEA)

Mannitol (45.0 g) and $H_3PO_4$ (1.96 g) are dissolved into water for injectables (800 ml) in order to obtain the starting saccharose solution.

The bulk of DHEA (20 g) is added to the saccharose solution that, after the pH has been adjusted at 7.0 by means of 2.5 M NaOH, is brought to the final volume of 1,000 ml. The solution is filtered through a 0.22 μm Durapore sterile filter (Millipore). During the process, the solution temperature is kept between 4° and 8° C.

Filling up and Lyophilisation

The vials are filled up with 1 ml of DHEA sterile solution, transferred to the freeze dryer and cooled at −45° C. for 6 hours. The lyophilisation is started at the temperature of −45° C. with a vacuum of 0.07 mBar. The heating is performed according to the following scheme: +20° C. for 12 hours; then +35° C. until the end of the cycle.

TABLE 1

Effects of DHEA in the septic shock induced by LPS + D-Galactosamine, in mice

| | | | % cumulative survival | | | | | | |
|---|---|---|---|---|---|---|---|---|---|
| | | No. | 24 hrs | | 48 hrs | | 72 hrs | | 96 hrs | |
| Treatment, dose/mouse and route | | of mice | 1st exp | 2nd exp | 1st exp | 2nd exp | 1st exp | 2nd exp | 1st exp | 2nd exp |
| LPS 0.1 μg, i.p.[1] + D-Gal. 18 mg, i.p.[1] | None | 10 | 20 | 20 | 20 | 10 | 20 | 10 | 20 | 10 |
| | DHEA, i.p. 100 μg[2] | 10 | 20 | — | 20 | — | 20 | — | 20 | — |
| | DHEA, i.p. 500 μg[2] | 10 | 10 | — | 10 | — | 10 | — | 10 | — |
| | DHEA, i.p. 1000 μg[2] | 10 | — | 20 | — | 20 | — | 10 | — | 0 |
| | DHEA, i.p. 1500 μg[2] | 10 | — | 70[a] | — | 70[a] | — | 50 | — | 50 |
| | DHEA, i.p. 2000 μg[2] | 10 | 100[a] | 100[a] | 100[a] | 100[a] | 100[a] | 100[a] | 100[a] | 100[a] |

[1] Administered as a mixture at time 0;
[2] Administered 1 hour before LPS + D-Gal administration
[a] Significantly different from LPS + D-Gal controls (Fisher's exact test, one-tailed)
N.B. DHEA was vehicled in saline 10% rabbit serum

TABLE 2

Effects of CHO r-hTBP-1 and DHEA in septic shock induced by LPS + D-Galactosamine, in mice

| | | No. of | % cumulative survival | | | |
|---|---|---|---|---|---|---|
| Treatment, dose/mouse and route | | Mice | 24 hrs | 48 hrs | 72 hrs | 96 hrs |
| LPS, i.p. 0.1 μg.[1] + D-Gal. i.p. 18 mg.[1] | None | 10 | 10 | 10 | 10 | 10 |
| | r-hTBP-1 125 μg[2] | 10 | 50 | 50 | 50 | 50 |
| | DHEA 1000 μg, i.p.[3] | 10 | 0 | 0 | 0 | 0 |
| | DHEA 1500 μg, i.p.[3] | 10 | 40 | 40 | 20 | 20 |
| | DHEA 1000 μg, i.p.[3] + rhTBP-1 125 μg[2] | 10 | 90[a,b] | 90[a,b] | 90[a,b] | 90[a,b] |
| | DHEA 1500 μg, i.p.[3] + r-hTBP-1 125 μg[2] | 10 | 100[a,b,c] | 100[a,b,c] | 100[a,b,c] | 100[a,b,c] |

[1] Administered as a mixture at time 0;
[2] Administered at time 0 (i.v.), and at 3, 6 and 24 hours (s.c.) after LPS + D-Gal injection.
[3] Administered 1 hour before LPS + D-Gal administration;
[a] Significantly different from LPS + D-Gal controls;
[b] Significantly different from DHEA alone;
[c] Significantly different from r-hTBP-1 alone (Fisher's exact test, one-tailed)
N.B.-DHEA was vehicled in saline 10% rabbit serum.

TABLE 3

Effects of DHEA in the septic shock induced by LPS + D-Galactosamine, in mice

| | | | % cumulative survival | | | | | | |
|---|---|---|---|---|---|---|---|---|---|
| | | No. | 24 hrs | | 48 hrs | | 72 hrs | | 96 hrs | |
| Treatment, dose/mouse and route | | of mice | 1st exp | 2nd exp | 1st exp | 2nd exp | 1st exp | 2nd exp | 1st exp | 2nd exp |
| LPS 0.1 μg, i.p.[1] + D-Gal. 18 mg, i.p.[1] | None | 10 | 10 | 40 | 10 | 40 | 10 | 40 | 10 | 40 |
| | DHEA, i.p. 250 μg[2] | 10 | — | 20 | — | 20 | — | 20 | — | 20 |
| | DHEA, i.p. 500 μg[2] | 10 | 50 | 30 | 40 | 30 | 30 | 30 | 30 | 30 |
| | DHEA, i.p. 750 μg[2] | 10 | 40 | 50 | 40 | 50 | 40 | 50 | 40 | 50 |
| | DHEA, i.p. 1000 μg[2] | 10 | 80[a] | — | 60 | — | 60 | — | 60 | — |

[1]Administered as a mixture at time 0
[2]Administered at time 0
[a]Significantly different from LPS + D-Gal controls (Fisher's exact test, one-tailed)
N.B.: DHEA was vehicled in saline 10% rabbit serum

TABLE 4

Effects of CHO r-hTBP-1 and DHEA in the septic shock induced by LPS and D-Galactosamine, in mice

| | | No. of mice | % cumulative survival | | | |
|---|---|---|---|---|---|---|
| Treatment, dose/mouse and route | | | 24 hr | 48 hr | 72 hr | 96 hr |
| LPS 0.1 μg i.p.[1] + D-Gal 18 mg i.p.[1] | none | 20 | 25 | 25 | 25 | 25 |
| | r-hTBP-1, 62.5 μg[2] | 10 | 20 | 10 | 0 | 0 |
| | DHEA 250 μg[3] (NaCl 10% RS) | 10 | 30 | 30 | 30 | 30 |
| | DHEA 250 μg[3] (NaCl 10% RS) + r-hTBP-1 62.5 μg[2] | 10 | 60 | 50 | 50 | 50 |
| | DHEA 250 μg[3] (NaCl 10% PLE) | 10 | 40 | 30 | 30 | 30 |
| | DHEA 250 μg[3] (NaCl 10% PLE) + r-hTBP-1 62.5 μg[2] | 10 | 90[a,b,c] | 60[c] | 40[c] | 40[c] |

[1]Administered as a mixture at time 0
[2]Administered at time 0 (i.v.) and at 3, 6 and 24 hours (s.c.) after LPS + D-Gal. injection.
[3]Administered as a single injection at time 0 i.p.
[a]Significantly different from LPS + D-Gal. controls (Fisher's exact test, one-tailed).
[b]Significantly different from DHEA alone (Fisher's exact test, one-tailed).
[c]Significantly different form r-hTBP-1 alone (Fisher's exact test, one-tailed).
N.B. DHEA was vehicled in saline 10% rabbit serum (NaCl 10% RS) or in saline 10% phospholipid emulsion (NaCl 10% PLE).

TABLE 5

Effects of CHO r-hTBP-1 and DHEA in the septic shock induced by LPS + Galactosamine, in mice

| | | | No. of mice | % cumulative survival | | | | | | |
|---|---|---|---|---|---|---|---|---|---|---|
| | | | | 24 hrs | | 48 hrs | | 72 hrs | | 96 hrs | |
| | Treatment dose/mouse and route | | | 1st exp. | 2nd exp. | 1st exp. | 2nd exp. | 1st exp. | 2nd exp. | 1st exp. | 2nd exp. |
| LPS 0.1 μg, i.p.[1] + D-Gal. 18 mg, i.p.[1] | A | None | 10 | 10 | 10 | 10 | 10 | 10 | 10 | 10 | 10 |
| | B | NaCl 10% PLE | 10 | — | 11 (n = 9) | — | 11 (n = 9) | — | 11 (n = 9) | — | 11 (n = 9) |
| | C | r-hTBP-1 62.5 μg[2] | 10 | 90[a] | 70[a] | 80[a] | 40 | 70[a] | 30 | 70[a] | 30 |
| | D | DHEA 250 μg[3] | 10 | 40 | — | 30 | — | 30 | — | 30 | — |
| | E | DHEA 62.5 μg x4[4] | 10 | 40 | 40 | 40 | 40 | 40 | 40 | 40 | 40 |
| | F | DHEA 250 μg[3] + r-hTBP-1 62.5 μg[2] | 10 | 100[a,b] | — | 100[a,b] | — | 100[a,b] | — | 100[a,b] | — |

TABLE 5-continued

Effects of CHO r-hTBP-1 and DHEA in the septic shock induced by LPS + Galactosamine, in mice

|  |  | % cumulative survival | | | | | | | |
|---|---|---|---|---|---|---|---|---|---|
|  |  | 24 hrs | | 48 hrs | | 72 hrs | | 96 hrs | |
| Treatment dose/mouse and route | No. of mice | 1st exp. | 2nd exp. | 1st exp. | 2nd exp. | 1st exp. | 2nd exp. | 1st exp. | 2nd exp. |
| G  DHEA 62.5 μg x4$^{(4)}$ + r-hTBP-1 62.5 μg$^{(2)}$ | 10 | 100$^{a,b}$ | 90$^{a,b}$ | 100$^{a,b}$ | 90$^{a,b}$ | 100$^{a,b}$ | 80$^{a,c}$ | 100$^{a,b}$ | 80$^{a,c}$ |

Notes to Table 5
$^{(1)}$Administered as a mixture at time 0
$^{(2)}$Administered at time 0 i.v., and at time 3, 6 and 24 hours (s.c.)
$^{(3)}$Administered as a single injection at time 0 i.p.
$^{(4)}$Administered at time 0, 3, 6 and 24 hours i.p.
$^{a}$Significantly different from LPS + D-Gal. controls (Fisher's exact test, one-tailed).
$^{b}$Significantly different from DHEA alone (Fisher's exact test, one-tailed).
$^{c}$Significantly different from r-hTBP-1 alone (Fisher's exact test, one-tailed).
N.B. DHEA was vehicled in 10% phospholipid emulsion (NaCl 10% PLE)

TABLE 6

Statistical significance of r-hTBP-1 group vs. r-hTBP-1 + DHEA groups ($\chi^2$-test)

| | p level | |
|---|---|---|
| Observation times (hours post LPS + D-Gal injection) | r-hTBP-1 vs. r-hTBP-1 62.5 + DHEA 250$^{(1)}$ | r-hTBP-1 vs. r-hTBP-1 62.5 + DHEA 4 × 62.5$^{(1)}$ |
| 24 | 0.015 | 0.015 |
| 48 | 0.022 | 0.0006 |
| 72 | 0.024 | 0.0002 |
| 96 | 0.024 | 0.0002 |

(1) Doses are expressed as μg/mouse.

What is claimed is:

1. A method for treating lethal bacterial infections in a patient which comprises administering to said patient a tumour necrosis factor (TNF) receptor in combination with dehydroepiandrosterone (DHEA) simultaneously, separately or sequentially.

2. The method of claim 1, wherein the TNF receptor is TNF Binding Protein-2.

3. The method of claim 1, wherein the TNF receptor is TNF Binding Protein-1.

4. The method of claim 3, wherein the condition being treated is septic shock.

5. The method of claim 1, wherein the condition being treated is septic shock.

6. A pharmaceutical composition comprising a tumour necrosis factor (TNF) receptor, dehydroepiandrosterone (DHEA) and a pharmaceutically acceptable excipient.

7. The pharmaceutical composition of claim 6, wherein the TNF receptor is TNF Binding Protein-2.

8. The pharmaceutical composition of claim 6, wherein the TNF receptor is TNF Binding Protein-1.

* * * * *